United States Patent [19]

Williams et al.

[11] Patent Number: 4,768,012
[45] Date of Patent: Aug. 30, 1988

[54] SENSORS

[75] Inventors: David E. Williams, Abingdon; Peter McGeehin, Newbury, both of England

[73] Assignee: United Kingdom Atomic Energy Authority, England

[21] Appl. No.: 115,563

[22] Filed: Oct. 29, 1987

Related U.S. Application Data

[63] Continuation of Ser. No. 730,824, May 6, 1985, abandoned.

[30] Foreign Application Priority Data

May 10, 1984 [GB] United Kingdom ................. 8411981

[51] Int. Cl.[4] .............................................. H01L 7/00
[52] U.S. Cl. ........................................ 338/34; 29/620
[58] Field of Search ...................... 338/34, 35; 73/335, 73/336; 29/620; 361/286; 428/201, 210

[56] References Cited

U.S. PATENT DOCUMENTS 3,550,057 12/1970 Yonng ............................ 338/35 X
4,276,128 6/1981 Nishino et al. ................. 73/335 X
4,528,543 7/1985 Miyoshi et al. ..................... 338/35

OTHER PUBLICATIONS

Agnew, Jeremy, *Thick Film Technology, Fundalmentals and Applications in Microelectronics:* Hayden Book Company, Inc.: New Jersey, 1973, pp. 32–42.

Primary Examiner—E. A. Goldberg
Assistant Examiner—M. M. Lateef
Attorney, Agent, or Firm—Larson and Taylor

[57] ABSTRACT

A moisture sensor which includes a moisture sensitive material and electrodes in communication with the moisture sensitive material, the moisture sensitive material containing a substantially electrically insulating substance derived from a colloidal dispersion and, distributed in or on the substance, an electrically conducting substance.

19 Claims, 3 Drawing Sheets

SENSORS

This application is a continuation of application Ser. No. 730,824, filed May 6, 1985, now abandoned.

FIELD OF THE INVENTION

The present invention relates to sensors and more particularly to moisture sensors suitable for use in gases and gaseous mixtures.

SUMMARY OF THE INVENTION

The present invention relates to a moisture sensor, a method for preparing a moisture sensor and a method for effecting determinations of moisture, all of which include the concept or usage of a moisture sensor comprising a moisture sensitive material and electrodes in communication with the moisture sensitive material; wherein the moisture sensitive material comprises a first, inorganic substantially electrically insulating substance derived from a colloidal dispersion and, distributed in or on the first substance, a second, electrically conducting substance.

BRIEF DESCRIPTION OF THE DRAWINGS

The present invention will now be further described, by way of a description of the preferred embodiments, specific examples and with reference to the accompanying drawings in which.

DETAILED DESCRIPTION OF THE INVENTION

Figure 1:
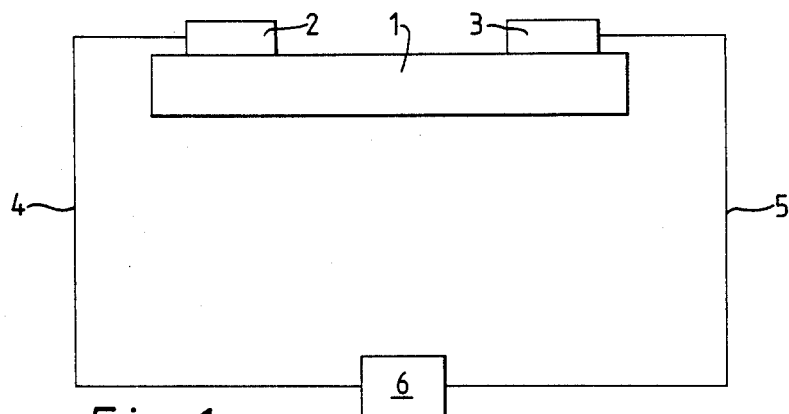
FIG. 1 is a diagrammatic representation of one form of moisture sensor in accordance with the present invention.

According to one aspect of the present invention there is provided a moisture sensor which sensor includes a moisture sensitive material and electrodes in communication with the moisture sensitive material, the moisture sensitive material comprising a first, substantially electrically insulating substance derived from a colloidal dispersion and, distributed in or on the first substance, a second, electrically conducting substance.

The first substance may, optionally, contain a dopant in addition to the second substance; thus the moisture sensitive material may comprise, for example, a first, substantially electrically insulating substance derived from a colloidal dispersion, a second, electrically conducting substance distributed in or on the first substance and a dopant dispersed in the first substance.

In one embodiment of the present invention a moisture sensor comprises a moisture sensitive material comprising a first, substantially electrically insulating substance derived from a colloidal dispersion and, distributed in or on the first substance, a second, electrically conducting substance and two or more electrodes in communication with the said moisture sensitive material and said moisture sensitive material is arranged so as to be capable of being contacted with moisture in a gas or gaseous mixture.

The first, substantially electrically insulating material may be for example alumina, zirconia, titania or silica.

The second, electrically conducting material may be for example, finely divided silver, copper, gold, platinum, palladium or carbon.

The dopant may be, for example, an oxide of potassium, of sodium, of lithium, of magnesium, of calcium, of cerium, of iron, of cobalt or of nickel.

A dopant may be, for example, one which enhances moisture response (e.g. K). A dopant may be, for example, one which can promote adhesion of a moisture sensitive material to a substrate.

A moisture sensor in accordance with the present invention may be used in quantitative and/or qualitative determinations of moisture in gases or gaseous mixtures. A moisture sensor in accordance with the present invention may be used as a humidity sensor (e.g. for measuring relative humidity).

The electrodes may be in direct communication with the moisture sensitive material by being in contact therewith.

In this Specification the term "gas" embraces a gas as such and any material which may be present in a gaseous phase, one example of which is a vapour.

Also, in this Specification the term "moisture sensitive material" means a material which is moisture sensitive in respect of an electrical property of the material. As used in this Specification "moisture" embraces water vapour, steam and water dispersed (e.g. entrained as fine droplets) in a gas or gaseous mixture.

It will be appreciated that the resistance and/or capacitance and/or impedance of the moisture sensitive material depends upon the amount of moisture contacting the moisture sensitive material. Thus, by measuring the resistance and/or capacitance and/or impedance of the moisture sensitive material the moisture in a gas or gaseous mixture can be sensed.

Since the resistance and/or capacitance and/or impedance of the moisture sensitive material tends also to be temperature dependant, the moisture sensor also preferably includes a temperature sensing means.

The moisture sensor may also, optionally, include a heating means to enable operating temperature to be adjusted and/or contaminants (e.g. organic contaminants) to be burnt off and/or condensed water to be evaporated from the moisture sensor if required.

It is to be understood that the sensitivity of a moisture sensitive material within the general formula hereinbefore will depend upon the composition of the moisture sensitive material. Thus, by selection of the composition of the moisture sensitive material its moisture response may be chosen.

The resistance and/or conductance and/or impedance may be measured directly. Alternatively, the measurement may be carried out indirectly by incorporating the moisture sensor in a feedback circuit of an oscillator such that the oscillator frequency varies with moisture content. Moisture content may then be determined using an electronic counter. The signal thus produced may be used to modulate a radio signal and thereby be transmitted over a distance (e.g. by telemetry or as a pulse train along an optical fibre).

An example of a gaseous mixture in which moisture sensing may be effected using a moisture sensor in accordance with the present invention is air.

According to another aspect of the present invention there is provided a method for the preparation of a moisture sensor which includes forming a moisture sensitive material comprising a first, substantially electrically insulating substance derived from a colloidal dispersion and, distributed in or on the first substance, a second, electrically conducting substance and providing electrodes in communication with the moisture sensitive material.

The moisture sensitive material optionally may be formed so as also to include a dopant.

A colloidal dispersion from which the first substance may be derived may be, for example, a sol of alumina, a sol of silica, a sol of titania or a sol of zirconia. The colloidal dispersion may be for example a mixed sol, for example, a mixed sol of alumina and titania. If desired the sol may be one which leads to a non-densifiable gel on conversion from sol to gel. If desired the sol may be one which enables a desired microstructure (e.g. a particular pore size distribution) to be produced in the moisture sensitive material.

By way of example, in accordance with one embodiment of the present invention the pore size distribution may be selected so as to minimise or substantially avoid hysteresis in moisture sensor response which may be caused by condensation of water in pores (e.g. during temperature cycling or relative humidity cycling).

Pore size distribution may be influenced by the choice of characteristics of the colloidal dispersion (e.g. particle size in the colloidal dispersion) and/or by selection of the processing conditions (e.g. drying treatment).

The second electrically conducting substance may be for example, silver, copper, gold, platinum, palladium or carbon and may, for example, be in the form of a colloidal dispersion which can be mixed with a colloidal dispersion from which the first substance may be derived.

Dopants optionally may be added to a colloidal dispersion from which the first substance may be derived. Thus, for example, potassium, sodium, lithium, magnesium, calcium, iron, cobalt or nickel may be added in the form of a soluble salt (e.g. a nitrate) thereof.

According to a further aspect of the present invention there is provided a method for effecting determinations of moisture in a gas or gaseous mixture which comprises contacting a moisture sensor with the gas or gaseous mixture and measuring the electrical response of the moisture sensor, said moisture sensor including a moisture sensitive material and electrodes in communication with the moisture sensitive material, the moisture sensitive material comprising a first substantially electrically insulating substance derived from a colloidal dispersion and, distributed in or on the first substance, a second electrically conducting substance.

In one embodiment of the immediately preceding aspect of the present invention the moisture sensor comprises a moisture sensitive material comprising a first substantially electrically insulating substance derived from a colloidal dispersion and, distributed in or on the first substance, a second electrically conducting substance and two or more electrodes in communication with the said moisture sensitive material, said moisture sensitive material and said electrodes being in contact with moisture in the same gas or gaseous mixture.

It is preferred that the moisture sensitive material has porosity to give a satisfactorily large surface area for contacting moisture.

The moisture sensitive material may, for example, be prepared from a mixture which includes a colloidal dispersion of a first, substantially electrically insulating substance and a second electrically conducting substance (and optionally a dopant or a precursor for a dopant).

The formation of the moisture sensitive material may be carried out in any convenient way. Thus, for example, a colloidal dispersion of a first electrically substantially insulating substance (or a precursor for the first substance) and a second substantially electrically conducting substance (or a precursor for the second substance) (and optionally a dopant or precursor for a dopant) may be treated to effect a sol-gel transformation (e.g. by drying or chemical gelation) and subsequently heated at a suitable temperature.

A moisture sensitive material in powder form for subsequent calcination may be prepared, for example, by spray drying a colloidal dispersion containing the first and second substances or precursors therefor (and optionally a dopant, or a precursor therefor) in appropriate proportions.

Moisture sensitive material (comprising a first substantially insulating substance derived from a colloidal dispersion and distributed therein or thereon a second, electrically conducting substance (and optionally a dopant)) in fine powder form may be pressed (e.g. with the optional addition of a binder, such as a solution of starch or PVA) into any suitable shape (e.g. a pellet) for use in a sensor in accordance with the invention.

The pressing may be followed by firing preferably at a temperature sufficiently high to give a solid body of moisture sensitive material but not so high as to destroy, to any significant extent, pore structure or surface state of the moisture sensitive material.

For example, firing may be effected at a temperature in the range 400° C.–900° C. A preferred range is 500° C. to 800° C.

In addition to assisting binding the powder into the desired shape the binder also burns out during the firing stage and may give rise to porosity or additional porosity.

Electrodes may be applied to the moisture sensitive material once prepared in any suitable manner. For example, electrodes (e.g. gold electrodes) may be applied by means of screen printing or sputtering.

Alternatively to preparing a moisture sensor by forming a pellet and applying electrodes as disclosed above, a sensor in accordance with the present invention may be formed in any suitable manner. Thus, for example, a parallel plate configuration may be fabricated by applying a first electrode (e.g. of gold) to an insulating substrate (e.g. by screen printing or sputtering), forming a moisture sensitive material layer covering at least a portion of the first electrode (e.g. by deposition, for example by screen printing or doctor-blading, from a dispersion and firing at a temperature in the range 450°–950° C. to promote adhesion and mechanical integrity) and forming a second electrode (e.g. of gold) on the moisture sensitive material layer (e.g. by screen printing or sputtering).

The second electrode is preferably permeable to facilitate access of gas or gaseous mixture in which the sensor is to be used to the moisture sensitive material layer.

By way of further example, a coplanar configuration can be used in the preparation of a sensor in accordance with the presen invention.

In such a coplanar configuration interdigitated electrodes (e.g. of gold) may be formed on an insulating substrate (e.g. by screen printing, or by sputtering, or by photolithography and etching). The interdigitated electrodes are subsequently covered with a moisture sensitive material layer (e.g. by means of deposition, for example by screen printing or doctor-blading, from a a colloidal dispersion) and firing at a temperature in the range of 450°–950° C. to promote adhesion and mechanical integrity.

Moisture sensors in accordance with the present invention fabricated in a coplanar configuration may include another layer or layers interposed between the moisture sensitive material layer and the electrodes. By way of example, an interposed layer may be a layer of a dielectric material, or a layer for promoting adhesion of the moisture sensitive material (e.g. a layer of glass material or a layer fabricated from a powder prepared from a gel).

By way of further example, a layer for promoting adhesion may be interposed between a dielectric layer and the moisture sensitive material layer. It will be appreciated that in a moisture sensor fabricated in this way a direct electrical contact to the moisture sensitive material layer is not made. The response may be detected by measuring changes in the impedance of the sensor to an alternating current caused by changes in the sheet resistance of the moisture sensitive material layer, which has a capacitance contact to the electrodes. Such a configuration as this may be used to reduce problems of poor contact and may assist in promoting the adhesion of the moisture sensitive material layer.

By way of further example, moisture sensors in accordance with the present invention may be fabricated by depositing a moisture sensitive material layer on electrodes of any suitable configuration for example those fabricated in the form of "wander tracks". By way of yet further example, a moisture sensitive material layer may be deposited onto a semi-conductor device such as a field effect transistor, MOS capacitor or gate-controlled diode.

By way of example a method in accordance with British Patent Application No. 8400503 (UKAEA) may be used in the preparation of a moisture sensor in accordance with the present invention.

British Patent Application No. 8400503 (UKAEA) discloses, inter alia, a method of preparing a coated substrate which comprises contacting a substrate with a dispersion of a gel powder of a ceramic material in a liquid organic medium of controlled rheology and having a non-volatile component, and drying the dispersion to give a coating comprising the ceramic material in the form of a gel and said non-volatile component. The coating may be fired to form a ceramic layer.

Thus, for example, a moisture sensitive material in powder form, as hereinbefore disclosed, may be mixed with a suitable liquid organic medium to form an "ink" suitable for screen printing or doctor blading.

By way of example, powders suitable for use in preparing sensors in accordance with the present invention have been prepared having compositions of $Al_2O_3$, 5 mol % $CeO_2$ and 0.1 to 10 mol % gold. Such powder may be prepared by forming a mixture of an alumina sol (formed by dispersing in water a finely divided alumina powder prepared by a vapour phase condensation method), a ceria sol (in accordance with BP No. 1603794) and chloroauric acid, and spray drying the mixture.

By way of further example coating dispersions for use in the preparing of sensor in accordance with the present invention have been prepared by mixing a ceramic powder derived from a colloidal dispersion ($Al_2O_3$, 5 mol % ceria) with colloidal gold in a screen printing medium. Coating dispersions of $Al_2O_3$, 5 mol % $CeO_2$ with 10 to 40 weight % gold have been formed by way of example.

The present invention will now be further described, by way of example only, as follows:

EXAMPLE 1

An aqueous colloidal dispersion (formed by dispersing in water a finely divided alumina powder provided by a vapour phase condensation method) was spray dried to give a powder comprising substantially spherical gel particles.

A quantity of this powder (0.3 g) was mixed with an equal weight of a screen printing medium (type R16 ex Electro Materials Corporation of America (EMCA)) and a thinner added (EMCA type 55) to give a viscous, semi-fluid coating dispersion.

The screen printing medium had an approximate composition (by weight) of: organic binder 7%, organic solvent 50% plasticiser 40% and surfactant 3%.

A gold flag electrode was applied to an alumina substrate (by screen printing) and the coating dispersion was doctor bladed onto the substrate so as to cover the electrode. The resulting coated substrate and electrode was dried in air and heated at 500° C. to produce from the coating dispersion a ceramic coating and a further gold electrode was applied to the ceramic coating by sputtering.

The coated substrate and electrodes were subsequently immersed in a colloidal suspension of silver in acetone, removed dried and fired to provide silver impregnation.

The electrodes were connected to a suitable electrical circuit and the response of the sensor was investigated. Results of resistance against relative humidity at 20° C. are given hereinafter in FIG. 5.

EXAMPLE 2

An aqueous colloidal dispersion of alumina doped with potassium nitrate (male ratio $K_2O/Al_2O_3=0.05$) was prepared by dispersing in water a finely dried alumina powder prepared by a vapour phase condensation method and adding $KNO_3$.

This aqueous colloidal dispersion was spray dried to give a powder comprising substantially spherical gel particles. A quantity (0.3 g) of this powder was mixed with an equal weight of type R16 (EMCA) screen printing medium of the kind used in Example 1 to form a coating dispersion.

Interdigitated silver electrodes were applied by screen printing to an alumina substrate and the coating dispersion was applied to the substate by means of screen printing to cover the electrodes.

The coated substrate and electrodes were dried and fired as in Example 1 and treated to achieve Ag impregnation as in Example 1.

The electrodes were connected to a suitable electrical current and the response was investigated at 20° C. The results are given in FIG. 6 which plots resistance against relative humidity.

EXAMPLE 3

A mixture was formed by admixing an alumina sol (formed by dispersing in water a finely divided alumina powder prepared by a vapour phase condensation method), a ceria sol (in accordance with BP No. 1603794) and chloroauric acid ("gold chloride") and the mixture was spray-dried to give a powder. The relative proportions of the components of the mixture were chosen to give a composition of $Al_2O_3$, 5 mol % $CeO_2$, 1 mol % gold in the powder. The powder was formed into a coating dispersion in the manner described in Examples 1 and 2.

The coating dispersion was applied by doctor-blading onto a pair of interdigitated gold contacts formed on an alumina tile and the whole was fired at 500° C. to give a moisture sensor.

The resistance of the sensor varied with relative humidity as shown in Table I.

TABLE I

| Relative Humidity (%) (20° C.) | $Log_{10}$ (resistance, ohms) |
| --- | --- |
| 0 | 10.4 |
| 31 | 6.9 |
| 50 | 6.4 |
| 63 | 6.0 |
| 73 | 5.8 |
| 80 | 5.6 |

EXAMPLE 4

A coating dispersion of colloidal gold with a ceramic powder derived from a sol (alumina+5 mol % ceria) was prepared by mixing a dispersion of the ceramic powder in a screen printing medium with a gold screen printing ink (type 8836 gold paste from Electro Science Laboratories Ltd.).

The proportions were selected to give a coating dispersion of $Al_2O$, 5 mol % $CeO_2$ with 35 weight % gold.

The coating dispersion was coated by a doctor-blading technique over a gold flag electrode (formed by screen printing) on an alumina tile and the whole was fired at 800° C. A second electrode was formed by sputtering gold onto the top of the ceramic layer, formed by firing, thereby to form a moisture sensor.

The resistance of the sensor thus formed varied with relative humidity as shown in Table II.

TABLE II

| Relative Humidity (%) (20° C.) | $Log_{10}$ (resistance, ohms) |
| --- | --- |
| 0 | 8.9 |
| 31 | 7.7 |
| 50 | 7.3 |
| 73 | 6.9 |
| 86 | 6.3 |

It is thought that fluxing agents in the gold paste served to improve adhesion of the ceramic layer to the alumina tile.

Referring now to FIG. 1 of the drawings there is shown a moisture sensor comprising a moisture sensitive material 1 in accordance with the present invention and, in contact with the moisture sensitive material 1 gold electrodes 2 and 3. (The moisture sensitive material may be carried by a substrate (e.g. of alumina) (not shown)).

Conductors 4 and 5 are provided to connect the electrodes 2 and 3 respectively to electrical measuring means 6 for measuring the resistance and/or capacitance and/or impedance of the moisture sensitive material 1.

In operation a gas or gaseous mixture containing mixture is contacted with the moisture sensitive material 1.

The resistance and/or capacitance and or impedance is measured by the electrical measuring means 6. Changes in the moisture content of the gas or gaseous mixture which result in a change of resistance and/or capacitance and/or impedance are observed as changes in the resistance and/or capacitance and/or impedance recorded by the measuring means 6.

Figure 2:
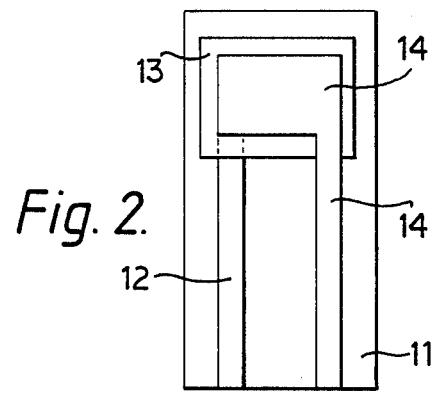
FIG. 2 and FIG. 2a represent diagrammatically a parallel plate moisture sensor in accordance with the present invention and a partially completed parallel plate sensor respectively.

Referring now to FIG. 2 of the drawings there is shown (in plan view) an insulating substrate 11 (e.g. an alumina ceramic tile) upon which is formed a first electrode 12 (e.g. of gold), a moisture sensitive material layer 13 comprising a moisture sensitive material prepared in accordance with the present invention and a second electrode 14 (e.g. of gold).

A parallel plate moisture sensor as shown in FIG. 2 may be fabricated by applying the first electrode 12 (e.g. of gold) to the insulating substrate 11 (e.g. by screen printing or sputering), forming a moisture sensitive material layer 13 covering at least a portion of the first electrode 12 (e.g. by deposition, (for example by screen printing or doctor-blading) from a colloidal dispersion (e.g. a dispersion or "ink" in accordance with British Patent Application No. 8400503) and firing at a temperature in the range 450°-950° C. to promote adhesion and mechanical integrity) and forming a second electrode 14 (e.g. of gold) on the moisture sensitive material layer 13 (e.g. by screen printing or sputtering).

Figure 2A:
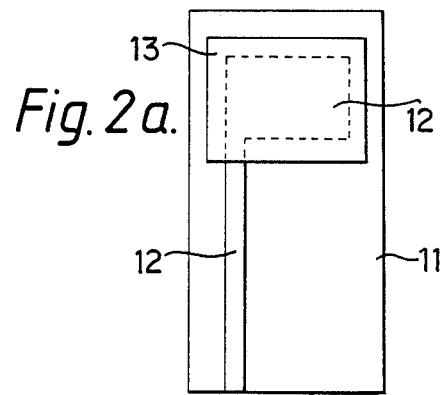

To facilitate understanding of the construction of the moisture sensor of FIG. 2 reference may be made to FIG. 2a which shows a parallel plate moisture sensor of the type shown in the FIG. 2 partially completed inasmuch as the second electrode 14 has not been formed. FIG. 2a thus shows the insulating substrate 11, the first electrode 12 and the moisture sensitive material layer 13 and it can be seen that the portion of the first electrode 12 covered by the moisture sensitive material layer 13 may extend in area to substantially the same extent as the second electrode 14.

In operation the first electrode 12 and second electrode 14 are connected to an electrical measuring means (not shown) for measuring the resistance and/or capacitance and/or impedance of the moisture sensitive material layer 13 and the moisture sensor is contacted with a gas or gaseous mixture containing moisture. The resistance and/or capacitance and/or impedance is measured by the electrical measuring means and changes in the moisture content of a gas or gaseous mixture which result in a change of resistance and/or capacitance and/or impedance are observed as changes in the resistance and/or capacitance and/or impedance recorded by the measuring means.

Figure 3:
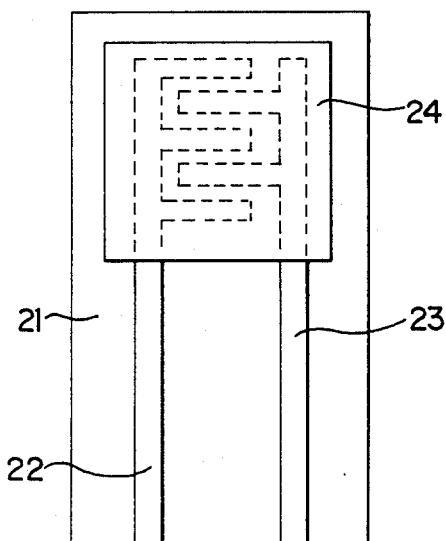
FIG. 3 is a diagrammatic representation of a coplanar moisture sensor in accordance with the present invention.

Referring now to FIG. 3 there is shown (plan view) an insulating substrate 21 (e.g. an alumina ceramic tile) upon which are formed electrodes 22 and 23 (e.g. both of gold), and a moisture sensitive material layer 24 (comprising a moisture sensitive material prepared in accordance with the present invention) covering at least a portion of both electrodes 22 and 23. It will be seen from the lines shown in dotted form in FIG. 3 the portions of the first electrode 22 and second electrode 23 covered by the moisture sensitive material layer 24 are interdigitated.

The first electrode 22 and the second electrode 23 may be provided on the insulating substrate 21 any suitable method. For example the methods disclosed for providing electrodes 2 and 14 in the parallel plate sensor described hereinbefore with reference to FIG. 2 and FIG. 2a may be used.

The moisture sensitive material layer 24 shown in FIG. 3 may be prepared by any suitable method. For example the methods disclosed for preparing moisture sensitive material layer 13 in FIG. 2 and FIG. 2a may be used.

Figure 4:
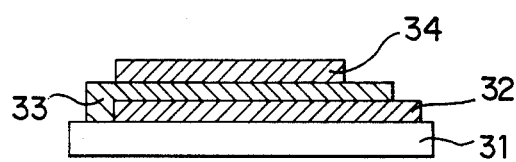
FIG. 4 is a diagrammatic representation of a further form of moisture sensor in accordance with the present invention.

Referring now to FIG. 4 of the drawings there is shown a diagrammatic representation in cross-section of a moisture sensor having an insulating substrate 31, electrodes represented as 32, a dielectric layer 33 and a moisture sensitive material layer 34 prepared in accordance with the present invention.

The electrodes 32 and the layers 33 and 34 may be prepared by any suitable method. Thus, for example, screen printing or sputtering or photolithography and etching may be used as is appropriate.

Figure 5:
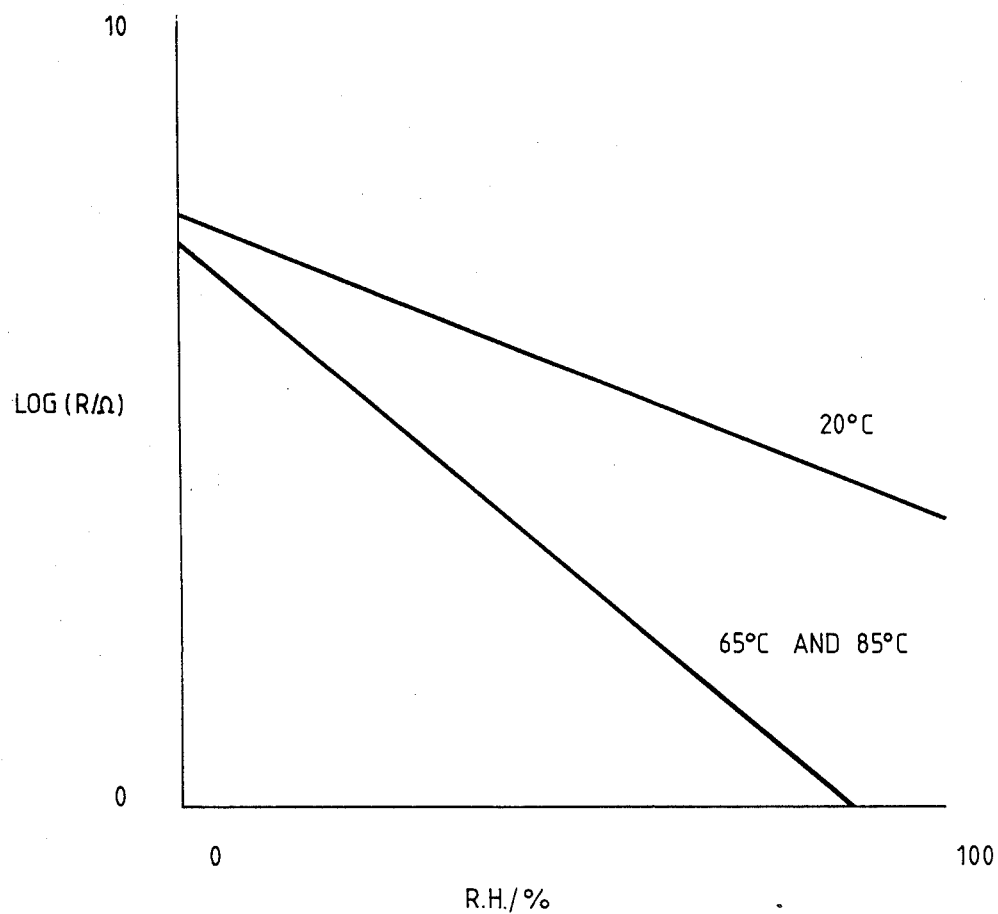
FIG. 5 is the humidity response, in terms of resistance against relative humidity, of a moisture sensor of the form prepared in Example 1 subjected to a cycle of relative humidity from low to high and back to low and to termperature variation in the sequence 20° C., 65° C., 20° C., 65° C., 20° C., 85° C., 20° C.
Figure 6:
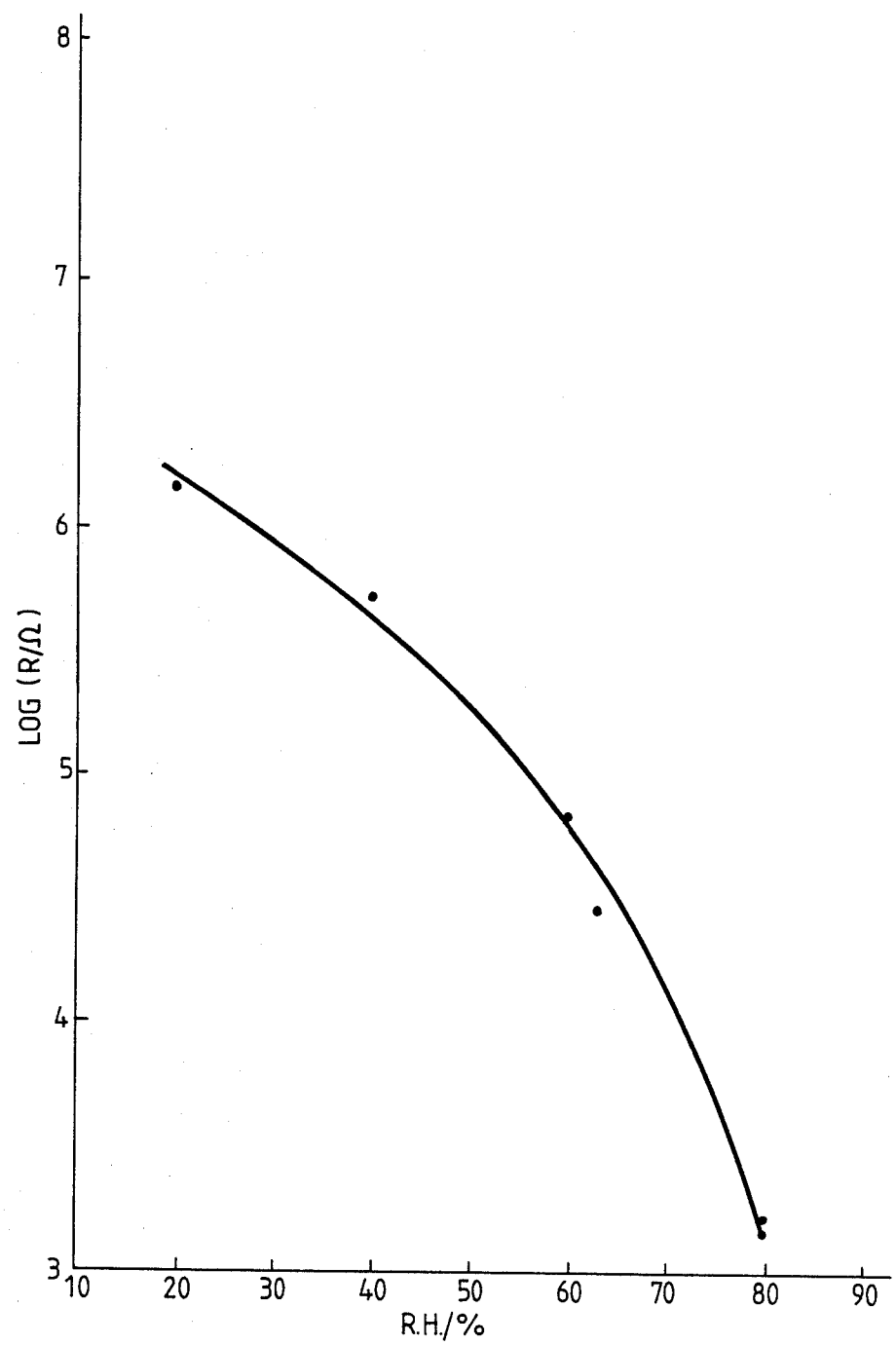
FIG. 6 is the response, in terms of resistance against relative sensor of the form prepared in Example 2.

Referring now to FIGS. 5 and 6 of the drawings there is shown respectively the humidity response of moisture sensors of the form prepared in Examples 1 and 2. In relation to FIG. 5 it will be noted that although the moisture sensor was subjected to relative humidity cycling and temperature cycling the hysteresis is negligible.

We claim:

1. A moisture sensor which sensor includes a moisture sensitive material and electrodes in communication with the moisture sensitive material, the moisture sensitive material comprising a first, substantially electrically insulating porous ceramic substance derived from a colloidal dispersion and, distributed throughout the first substance, a second, finely divided electrically conducting substance.

2. A moisture sensor as claimed in claim 1 further comprising tow or more electrodes in communication with the said moisture sensitive material, said moisture sensitive material being arranged so as to be capable of being contacted with moisture in a gas or gaseous mixture.

3. A moisture sensor as claimed in claim 1 wherein the first, substantially electrically insulating substance is alumina, zirconia, titania or silica.

4. A moisture sensor as claimed in claim 1 wherein the second, electrically conducting material is selected from the group consisting of finely divided silver, copper, gold, platinium, palladium and carbon.

5. A moisture sensor as claimed in claim 1 wherein the first, substantially electrically insulating substance contains a dopant.

6. A moisture sensor as claimed in claim 5 wherein the dopant is an oxide of potassium, of sodium, of lithium, of magnesium, of calcium, of cerium, of iron, of cobalt or of nickel.

7. A moisture sensor as claimed in any one of claim 1 wherein the sensor includes a temperature sensing means.

8. A moisture sensor as claimed in any one of claim 1 wherein the sensor includes heating means.

9. A method for the preparation of a moisture sensor which includes forming a moisture sensitive material comprising a first, substantially electrically insulating porous ceramic substance derived from a colloidal dispersion and distributed througout the first substance, a seocnd finely divided electrically conducting substance and providing electrodes in communication with the moisture sensitive material.

10. A method as claimed in claim 9 wherein the first, substantially electrically insulating substance is derived from a sol selected from the group consisting of an alumina sol, a silica salt, a titania sol and a zirconia sol.

11. A method as claimed in claim 9 wherein the first, substantially electrically insulating substance is derived from a mixed sol.

12. A method as claimed in claim 9 wherein a colloidal dispersion selected from the group consisting of a colloidal dispersion of silver, of copper, of gold, of platinium, of palladium and of carbon is used to provide a second, electrically conducting substance.

13. A method as claimed in claim 9 wherein a dopant is introduced in the form of a soluble salt.

14. A method as claimed in claim 9 wherein formation of moisture sensitive material includes treating a colloidal dispersion to effect a sol-gel transformation.

15. A method as claimed in claim 9 wherein formation of the moisture sensitive material includes spray drying a colloidal dispersion.

16. A method as claimed in claim 9 wherein formation of the moisture sensitive material includes pressing to a suitable shape followed by heating 17. A method as claimed in claim 9 wherein formation of the moisture sensitive material and/or providing the electrodes includes a screen-printing step or a doctor-blading step.

18. A method for effecting determinations of moisture in a gas or gaseous mixture which comprises contacting a moisture sensor with the gas or gaseous mixture and measuring the electrical response of the moisture sensor, said moisture sensor including a moisture sensitive material and electrodes in communication with the moisture sensitive material, the moisture sensitive material comprising a first substantially electrically insulating porous ceramic substance derived from a colloidal dispersion and, distributed throughout the first substance, a second, finely divided electrically conducting substance.

19. A method for effecting determinations of moisture in a gas or gaseous mixture as claimed in claim 18 wherein the moisture sensor further comprises two or more electrodes in communication with the said moisture sensitive material, and said moisture sensitive material and said electrodes are in contact with moisture in the same gas or gaseous mixture.

* * * * *